United States Patent [19]

McKinnie et al.

[11] Patent Number: 5,208,389
[45] Date of Patent: May 4, 1993

[54] PROCESS FOR HIGH PURITY TETRABROMOBISPHENOL-A

[75] Inventors: Bonnie G. McKinnie; Gary L. Sharp, both of Magnolia, Ark.

[73] Assignee: Ethyl Corporation, Richmond, Va.

[21] Appl. No.: 861,544

[22] Filed: Apr. 1, 1992

[51] Int. Cl.$^5$ .................... C07C 39/367; C07C 37/68
[52] U.S. Cl. .................... 568/726; 568/722; 568/724; 568/725
[58] Field of Search ............... 568/722, 723, 724, 726

[56] References Cited

U.S. PATENT DOCUMENTS

| | | | |
|---|---|---|---|
| 3,029,291 | 4/1962 | Dietzler | 260/619 |
| 3,182,088 | 5/1965 | Hennis | 260/619 |
| 3,234,289 | 2/1966 | Hennis | 568/726 |
| 3,546,302 | 12/1970 | Asadorian et al. | 260/619 |
| 3,868,423 | 2/1975 | Montanari et al. | 260/619 A |
| 3,929,907 | 12/1975 | Janzon et al. | 260/619 R |
| 4,075,119 | 2/1978 | Schmidt et al. | 252/182 |
| 4,112,242 | 9/1978 | Swietoslawski et al. | 568/726 |
| 4,180,684 | 12/1979 | Kleinschmit et al. | 568/726 |
| 4,210,765 | 7/1980 | Mark | 568/726 |
| 4,283,566 | 8/1981 | Mark | 568/726 |
| 4,451,675 | 5/1984 | Bounds | 568/726 |
| 4,628,124 | 12/1986 | McKinnie et al. | 568/726 |
| 4,701,568 | 10/1987 | McKinnie et al. | 568/726 |
| 4,783,556 | 11/1988 | Mitchell et al. | 568/726 |
| 4,909,997 | 3/1990 | Mitchell et al. | 422/225 |
| 4,990,321 | 2/1991 | Sato et al. | 423/486 |
| 5,008,458 | 4/1991 | Telschow | 568/28 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/226 |
| 5,059,726 | 10/1991 | Eguchi et al. | 568/726 |
| 5,068,463 | 11/1991 | Walter | 568/726 |
| 5,107,035 | 4/1992 | Hines et al. | 568/726 |

FOREIGN PATENT DOCUMENTS

| | | |
|---|---|---|
| 0380363 | 1/1990 | European Pat. Off. |
| 2005259 | 8/1971 | Fed. Rep. of Germany |
| 7420082 | 1/1976 | France |
| 64410 | 3/1985 | Israel |
| 58728 | 5/1979 | Japan |
| 225034 | 12/1983 | Japan |
| 048641 | 3/1987 | Japan |
| 316748 | 12/1988 | Japan |
| 0196747 | 8/1990 | Japan |
| 949306 | 2/1964 | United Kingdom |

OTHER PUBLICATIONS

Chemical Abstract No. 174372c.
Chemical Abstract No. 177054b.
Chemical Abstract No. 186315h.
Chemical Abstract No. 189500c.
"Copolycarbonates of bisphenol-A and tetrahalobisphenol-A; Synthesis of Tetrahalobisphenols-A: Part I," Pop. Plast. Rubber 26(1), 3-9 (1981).
"Tetrahalogenated 4:4'-Dihydroxydiphenylalkanes, Their Synthesis and Some of Their Reactions," Egypt. J. Chem. 20, No. 5, pp. 483-490 (1977).
"Oxidative Bromination of 2,2-Bis (4'Hydroxyphenyl)-Propane," Institute of Organochlorine Synthesis, Academy of Sciences of the Azerbaidzhan SSR, Sumgait, (1989).
Chemical Abstracts 101 (26):231164p.
Chemical Abstracts 102 (8):62672d.
Chemical Abstracts 102 (10):79427a.
Chemical Abstracts 105 (18): 155068p.
Chemical Abstracts 109 (13): 110003e.
Chemical Abstracts 110 (20):173951d.

Primary Examiner—Werren B. Lone
Attorney, Agent, or Firm—David E. LaRose

[57] ABSTRACT

The quality of a product predominant in tetrabromobisphenol-A is enhanced by contacting the product with a quality enhancing amount of treated water and heat treating the product for a period of time and at a temperature which are sufficient to obtain a TBBPA predominant product having less than about 20 ppm of ionic impurities.

19 Claims, No Drawings

PROCESS FOR HIGH PURITY TETRABROMOBISPHENOL-A

BACKGROUND

This invention relates to an improvement in a process for enhancing the purity of a flame retardant product predominant in a tetrabromobisphenol-A.

4,4'-isopropylidenebis(2,6-dibromophenol) is a well known commercial flame retardant and is usually referred to as tetrabromobisphenol-A (hereinafter "TBBPA"). Products comprised predominantly of TBBPA are useful as flame retardants in many macromolecular formulations. The literature is replete with processes for the manufacture of TBBPA, see, for example, U.S. Pat. No. 3,029,291; U.S. Pat. No. 3,182,088; U.S. Pat. No. 3,234,289; U.S. Pat. No. 3,363,007; U.S. Pat. No. 3,546,302; U.S. Pat. No. 3,868,423; U.S. Pat. No. 3,929,907; U.S. Pat. No. 4,013,728; U.S. Pat. No. 4,036,894; U.S. Pat. No. 4,112,242; U.S. Pat. No. 4,180,684; U.S. Pat. No. 4,431,847; U.S. Pat. No. 4,451,675; U.S. Pat. No. 4,701,568; U.S. Pat. No. 4,990,321; U.S. Pat. No. 5,008,469; U.S. Pat. No. 5,059,726; Japanese Kokai 2 (1990) 196,747; EPO 380,363; British Patent 949,306. Processes which produce a TBBPA predominant product having a particularly low organic impurity content are described in U.S. Pat. No. 4,628,124; U.S. Pat. No. 4,783,556; U.S. Pat. No. 4,909,997; U.S. Pat. No. 5,017,728; and U.S. Pat. No. 5,059,722 incorporated herein by reference as if fully set forth. Most if not all of the foregoing processes describe the recovery of TBBPA from the reaction mass by adding water to precipitate the product.

While the processes described in the '124 '556, '728 and '722 patents yield products which are useful for most flame retardant applications, there exists a need for a TBBPA predominant product having both a low organic impurity and a low ionic impurity. These low impurity TBBPA predominant products have particular application as flame retardants in polymers and plastics for the electronics industry.

A particularly useful process for enhancing the quality of a product predominant in TBBPA is disclosed in co-pending application Ser. No. 614,372, filed Nov. 15, 1990, now allowed, which is incorporated herein by reference as if fully set forth.

THE INVENTION

A significant improvement in a process for enhancing the quality of a product predominant in tetrabromobisphenol-A has now been discovered. The improvement comprises (a) contacting the product with a quality enhancing amount of treated water and, (b) subsequently, heat treating the product for a period of time and at a temperature which are sufficient to obtain a TBBPA predominant product having less than about 20 ppm of total ionic impurity.

The improved process of the present invention provides, for the first time, a method for the production of a product predominant in tetrabromobisphenol-A (TBBPA) on a large scale at high yield having greatly reduced total ionic impurity. By greatly reduced is meant the ionic impurity in the recovered and dried product is preferably less than about 30 ppm, more preferably less than about 20 ppm, and most preferably less than about 10 ppm. For purposes of this invention, "total ionic impurity" means any of one or more of compounds represented by MBr wherein M is hydrogen, a metal, or an alkali or alkaline earth metal ion selected from the group consisting essentially of Ba, Ca, Fe, K, Na, Mg, and Mn. In a preferred embodiment, the ionic impurity is predominantly HBr (i.e. greater than about 50% by weight HBr).

The invention has particular application in providing a means for enhancing the quality of a TBBPA predominant having a low organic impurity content. However, the process of this invention may be applied to a TBBPA predominant product produced by any one or more prior art processes.

In another embodiment, this invention provides a flame retardant composition comprising a product predominant in tetrabromobisphenol-A and containing less than about 10 ppm total ionic impurity and less than about 3.0 percent total organic impurity.

In still another embodiment, this invention provides a process for preparing a flame retardant product predominant in tetrabromobisphenol-A comprising:

a) brominating bisphenol-A with bromine at a temperature in the range of from about 0° C. to about 100° C. in a solvent comprising methanol and from about 3 to about 15 wt. % water; b) collecting the brominated bisphenol-A product as a solid; c) contacting the solid product with a quality enhancing amount of treated water; and d) heat-treating the contacted solid at a temperature and for a period of time, which time and temperature are sufficient to form a product predominant in tetrabromobisphenol-A having less than about 20 ppm total ionic impurity.

A key feature of this invention is the step of contacting the TBBPA predominant product with a quality enhancing amount of treated water prior to heat treating the product. The treated water is characterized as having a resistivity of greater than about 50,000 ohms, more preferably, greater than about 100,000 ohms, and most preferably greater than about 500,000 ohms. Such treated water can be prepared by contacting the water with commercially available ion exchange resin until the resistivity of the so treated water is greater than about 50,000 ohms. Higher resistivities can be obtained by treating the water in any one or more commercially available reverse osmosis units and subsequently contacting the water with an ion exchange resin. In the latter case, resistivities of greater than 500,000 ohms, typically greater than 1,000,000 ohms may be obtained. While it is desirable to contact the TBBPA predominant product with treated water having a resistivity as high as economically reasonable, good results may be obtained by contacting the TBBPA product with treated water having a resistivity at least about 50,000 ohms. The methods of preparing treated water having the foregoing resistivities is well known by those skilled in the art.

The amount of treated water used in contacting the TBBPA predominant product is that amount sufficient to enhance the quality of the product to the desired degree. Preferably, the product is contacted with at least about 0.1 grams of treated water per gram of product. More preferably, the product is contacted with at least about 0.2 grams of treated water per gram of product, and most preferably with about 0.3 to about 0.5 grams of water per gram of product. There is no real upper limit on the amount of treated water to use in contacting the product, however, economic considerations and manufacturing equipment limitations provide that only the amount of water required to enhance the quality of product to the desired degree need be used.

While it may be beneficial to contact the product with treated water at any stage of the process for preparing TBBPA, in general, the contacting need only be done after or during the procedure for separating the TBBPA predominant product from the reaction mass slurry. The reaction mass slurry is formed, by adding sufficient water to the reaction mass to precipitate the TBBPA predominant product. Removal of byproduct methyl bromide prior to filtering the product slurry is desirable. Such removal may be accomplished by well known techniques. The separation of the TBBPA predominant product from the reaction mass slurry may be accomplished by filtering or centrifuging the product solids. In the filtering or centrifuging operation, a major amount of aqueous HBr is removed from the solid product in the centrate or filtrate. However, residual HBr impurity remains in the solid product obtained from the centrifuge. The residual HBr impurity contributes to the total ionic impurity in the solid product.

Another key feature of this invention is the step of heat treating the TBBPA predominant product at a temperature and for a period of time which are sufficient to reduce the amount of total ionic impurity in the thus treated product. When heat treating the product, the temperature is generally above about 110½°C. Preferably, the temperature is in a range of from about 120½°C. to about 180½°C., and most preferably in a range of from about 130½°C. to about 175½°C. Higher or lower temperatures may also be used. However, the temperature should not be so high as to cause melting or degradation of the TBBPA predominant product. At a temperature lower than the preferred temperature, a longer heating time may be required to achieve the desired results.

The heat treating time required to obtain the enhanced quality product is related to the temperature used for the heat treating. At a temperature above about 120° C., the time for heat treating the product is preferably greater than about 10 seconds. A preferred residence time for heat treating a product predominant in TBBPA ranges from about 30 seconds to about 1 hour with the most preferred time ranging from about 5 minutes to about 30 minutes.

The time required may also depend on the equipment selected for the heat treating process. Equipment which may be useful in the process of this invention include the Wyssmont Turbo-Dryer® and the Bepex Torusdisc® Dryer, e.g. Torusdisc® Model TDJ2611 having 218 square feet of heat transfer area and a 26 minute residence time at about 120° C. or the like. Those skilled in the art can readily select heat treating equipment based on the above residence times and temperatures in order to obtain the desired low impurity product.

Pressure is not critical to the process of this invention as the bromination reaction can be carried out at pressures ranging from subatmospheric to superatmospheric. It is less costly and more desirable to operate at about atmospheric pressure.

Particularly preferred processes for the production of a product predominant in TBBPA is described in Mitchell, et al., U.S. Pat. No. 4,783,556; U.S. Pat. No. 4,909,997; and U.S. Pat. No. 5,059,722; and McKinnie et al., U.S. Pat. No. 5,017,728 incorporated herein by reference. The process of the Mitchell et al. and McKinnie et al. patents produce a product generally having less than about 3 percent organic impurities. Typical organic impurities found in the product are partially brominated bisphenol compounds e.g. monobromobisphenol-A, dibromobisphenol-A and tribromobisphenol-A; partially brominated phenol compounds, e.g. bromophenol, dibromophenol, and tribromophenol; and brominated phenylphenols formed from traces of phenylphenol found in the bisphenol-A reactant. Traces of other organic compounds found in the TBBPA predominant product may include 1-bromo-2-(3,5-dibromo-4-hydroxyphenyl)-2-methoxypropane, 1,1-dibromo-2-(3,5-dibromo-4-hydroxyphenyl)-2-methoxypropane, and 1,3-dibromo-2-(3,5-dibromo-4-hydroxyphenyl)-2-methoxypropane.

While the organic impurities of the product produced by the Mitchell et al. ('556 and '997) and McKinnie et al. ('722 and '728) process are acceptably low for most flame retardant applications, the total ionic impurity in the product is typically about 60 ppm or more. It has now been discovered that TBBPA predominant product containing a total ionic impurity which is initially about 60 ppm or more can be treated by the process of this invention to obtain a TBBPA predominant product having less than about 30 ppm and most preferably, less than about 10 ppm total ionic impurity. When produced by the process of the Mitchell et al. or McKinnie et al. patents ('556, '997, '722, and '728), the TBBPA predominant product treated by the process of this invention also contains less than about 3.0 percent organic impurity.

The process of this invention may be used to reduce the total ionic impurity content of a TBBPA predominant product before or after drying the product. It is particularly preferred, to separate the product from the reaction mass prior to contacting the product with a quality enhancing amount of treated water and heat treating the product. Alternatively, the product may be dried and ground to a powder having an average particle size of about 70 microns or less before contacting the product with treated water and heat treating the product.

The following examples illustrate the features of this invention. For the purposes of this invention, plant process water is untreated water containing 150–200 ppm total dissolved solids.

EXAMPLE 1

Heat treatment without contacting with treated water

One vent of a lab oven was removed and a stirrer having an inverted ½ moon paddle was inserted into the oven through the vent. A 600 Ml beaker was placed into the oven and the beaker was preheated to about the oven temperature. TBBPA product (20 grams) produced by the process of the Mitchell et al. Patent, U.S. Pat. No. 4,783,556 was filtered, washed with plant process water and placed into the preheated beaker which was in the oven. During the heat treatment step, the product was stirred by hand. The product had an initial total ionic content of about 84 ppm HBr. The results of the heat treating runs are listed in Table I. Samples 1–8 were previously dried before heat treating. Samples 9–10 were still wet with water prior to heat treating and had an initial total ionic content of 74 ppm.

TABLE I

| Run No. | Time (min.) | Temp. (°C.) | Total Ionics (ppm) |
| --- | --- | --- | --- |
| 1 | 10 | 121–124[1] | 35 |
| 2 | 10 | 135–140[1] | 10 |
| 3 | 5 | 150–155[1] | 10 |

TABLE I-continued

| Run No. | Time (min.) | Temp. (°C.) | Total Ionics (ppm) |
|---|---|---|---|
| 4 | 5 | 135[2] | 10 |
| 5 | 0.5 | 135[2] | 49 |
| 6 | 1.5 | 140[2] | 10 |
| 7 | 4 | 127[2] | 15 |
| 8 | 4 | 105[2] | 31 |
| 9 | 2.2 | 135[2] | 24 |
| 10 | 2.1 | 140[2] | 16 |

[1]Oven temperatures.
[2]TBBPA product temperatures.

In Runs 11-20, about 5 pounds of dry TBBPA predominant product produced by the process described in the Mitchell et al. patent were washed with plant process water. The product initially contained about 59 to about 62 ppm total ionic impurity and was dried at various temperatures in the dryers indicated. Samples of the product during the drying cycle were analyzed and the results are given in the following Tables II and III.

TABLE II

| Run No. | Temp. (°C.)[3] | Time (min.) | Total Ionics (ppm) |
|---|---|---|---|
| Wyssmont Turbo-Dryer ® | | | |
| 11 | 121 | 10 | 58 |
|  |  | 15 | 55 |
|  |  | 20 | 50 |
|  |  | 25 | 46 |
|  |  | 30 | 35 |
| 12 | 132 | 10 | 53 |
|  |  | 14 | 49 |
|  |  | 18 | 42 |
|  |  | 22 | 35 |
|  |  | 26 | 27 |
| 13 | 143 | 10 | 51 |
|  |  | 14 | 48 |
|  |  | 20 | 26 |
|  |  | 30 | 14 |
| 14 | 160 | 10 | 44 |
|  |  | 14 | 33 |
|  |  | 20 | 18 |
|  |  | 30 | 11 |
| 15 | 143 | 18 | 50 |
|  |  | 30 | 22 |
|  |  | 40 | 13 |
|  |  | 60 | 10 |
| 16 | 177 | 10 | 48 |
|  |  | 15 | 19 |
|  |  | 20 | 15 |
|  |  | 25 | 10 |
|  |  | 30 | 8 |

[3]Dryer air temperature.

TABLE III

| Run No. | Temp. (°C.)[3] | Time (min.) | Total Ionics (ppm) |
|---|---|---|---|
| Bepex Torusdisc ® Dryer | | | |
| 17 | 149 | 5 | 49 |
|  |  | 9 | 41 |
|  |  | 11 | 34 |
|  |  | 18 | 21 |
|  |  | 31 | 20 |
| 18 | 177 | 3 | 39 |
|  |  | 6 | 22 |
|  |  | 10 | 17 |
|  |  | 50 | 14 |
| 19 | 163 | 6 | 29 |
|  |  | 8 | 19 |
|  |  | 12 | 15 |
|  |  | 22 | 19 |
|  |  | 30 | 11 |
| 20 | 149 | 3 | 47 |
|  |  | 5 | 32 |
|  |  | 10 | 24 |
|  |  | 13 | 20 |
|  |  | 15 | 15 |
|  |  | 30 | 12 |

[3]Dryer steam temperature.

EXAMPLE 2

Heat treatment without contacting with treated water

A sample of TBBPA product (100 grams) produced generally in accordance with the process of Mitchell et al. U.S. Pat. No. 4,783,556 having 66 ppm total ionics was slurried in 20 wt. % methanol in plant process water. The TBBPA product was then filtered from the slurry and washed with about 200 mL of plant process water. After washing the product, the product was heat treated at 140° C. for 2.5 days. Total ionics after the heat treating step was 30 ppm.

EXAMPLE 3

Heat treatment without contacting with treated water

Tetrabromobisphenol-A was prepared generally in accordance with U.S. Pat. No. 4,783,556. A reaction flask was charged with 84.3 grams of bisphenol-A, and 500 mL of methanol. Bromine (79 mL) was added to the refluxing methanol over a period of 1 hour. The resulting reaction mass was stirred for 20 minutes while refluxing. Plant process water (170 mL) was added to precipitate the product and form a product slurry. The TBBPA product was then filtered from the slurry and washed with about 200 mL of 20 wt. % methanol then 200 mL of plant process water. The washed product was reslurried in about 200 mL of 20 wt. % methanol in plant process water, filtered, and washed with about 20 mL of plant process water. Analysis of the washed wet cake indicated that the TBBPA product had a total ionic content of 40 ppm. The product was then heat treated at 140° C. for 16 hours. Total ionics after heat treating was 27 ppm.

EXAMPLE 4

Product contacted with treated water then heat treated

A sample of TBBPA product (100 grams) produced generally in accordance with the process of Mitchell et al. Patent, U.S. Pat. No. 4,783,556 having 66 ppm total ionics was slurried in 20 wt. % methanol in deionized water having a resistivity of about 100,000 ohms. The TBBPA product was then filtered from the slurry and washed with 200 mL of deionized water having a resistivity of about 100,000 ohms. After washing the product, the product was heat treated at 140° C. for 2.5 days. Total ionics after the heat treating step was less than 2 ppm.

EXAMPLE 5

Product contacted with treated water then heat treated

A sample of TBBPA product (100 grams) produced generally in accordance with the process of Mitchell et al. U.S. Pat. No. 4,783,556 having 62 ppm total ionics was slurried in 10 wt. % methanol in deionized water having a resistivity of about 100,000 ohms. The TBBPA product was then filtered from the slurry and washed with about 200 mL of deionized water having a resistivity of about 100,000 ohms. After washing the product, the total ionics were 46 ppm. The sample was separated into three portions and heat treated at different temperatures. Analysis of the product contacted with treated water and subsequently heat treated are given in Table IV.

TABLE IV

| Sample | Temperature (°C.) | Time (Hrs) | Total Ionics (ppm) |
|---|---|---|---|
| 1 | 120 | 4 | <8 |
| 2 | 60–65 | 5 | 49 |
| 3 | 70 | 22 | 40 |
| 4 | 120 | 22 | <2 |

The process of this invention is applicable to flame retardant products comprised predominantly of brominated compounds derived from compounds represented by the following:

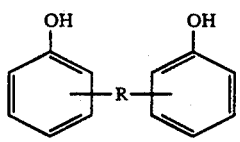

wherein R is a divalent aliphatic hydrocarbon group of 1–4 carbon atoms or a direct bond between two benzene rings. Representative examples are 4,4'-methylenebisphenol; 2,2'-methylenebisphenol; 2,4'-methylenebisphenol; 4,4'-ethylidenebisphenol; 2,2'-ethylidenebisphenol; 2,4'-ethylidenebisphenol; 2,2'-isopropylidenebisphenol; 2,4'-isopropylidenebisphenol; 4,4'-butylidenebisphenol; 2,2'-butylidenebisphenol; 4,4'-bisphenol; 2,2'-bisphenol; 2,4'-bisphenol and the like. These bisphenols can be substituted for the bisphenol-A, i.e., 4,4'-isopropylidenebisphenol, used in the foregoing description and examples of the present invention. All of the brominated products can be used as fire retardants in a broad range of organic materials normally susceptible to combustion in the presence of air and an ignition source.

Other variations are possible within the spirit and scope of the appended claims.

What is claimed is:

1. An improvement in a process for enhancing the quality of a flame retardant product predominant in tetrabromobisphenol-A (TBBPA), wherein the improvement comprises (a) contacting said product with an amount of treated water, which treated water has a resistivity of greater than about 50,000 ohms and (b) heat treating said product for a period of time and a temperature which are sufficient to obtain a TBBPA predominant product having less than about 20 ppm of total ionic impurity wherein the amount of treated water is more than about 0.2 grams per gram of product so contacted and wherein the ionic impurity is predominantly HBr.

2. The improvement of claim 1 wherein the temperature is in a range of from about 120° C. to about 170° C.

3. The improvement of claim 1 wherein the time is in a range of from about 30 seconds to about 1 hour.

4. The improvement of claim 1 wherein the treated water has a resistivity of greater than about 100,000 ohms.

5. The improvement of claim 1 wherein the tetrabromobisphenol-A product to be heat treated is an essentially dry powder.

6. The improvement of claim 1 wherein the amount of treated water is more than about 0.3 grams of water per gram of product so contacted.

7. The improvement of claim 2 wherein the time is in a range of from about 30 seconds to about 1 hour.

8. The improvement of claim 1 wherein the tetrabromobisphenol-A product to be heat treated is an essentially dry powder.

9. The improvement of claim 1 wherein the treated water has a resistivity of greater than about 100,000 ohms.

10. The improvement of claim 1 wherein the amount of ionic impurity in the contacted and heat treated product is less than about 10 ppm.

11. A flame retardant composition comprising a product predominant in tetrabromobisphenol-A and containing less than about 10 ppm ionic impurity and less than about 2.0 percent organic impurity.

12. The composition of claim 11 having less than about 5 ppm of ionic impurity.

13. A process for preparing a flame retardant product predominant in tetrabromobisphenol-A comprising:
 a) brominating bisphenol-A with bromine at a temperature in the range of from about 0° C. to about 100° C. in a solvent comprising methanol and from about 3 to about 15 wt. % water;
 b) collecting the brominated bisphenol-A product as a solid;
 c) contacting the solid product with an amount of treated water, which treated water has a resistivity of greater than about 50,000 ohms; and
 d) heat treating the contacted solid at a temperature and for a period of time, which time and temperature are sufficient to form a product predominant in tetrabromobisphenol-A having less than about 20 ppm total ionic impurity wherein the amount of treated water is more than about 0.2 grams per gram of solid product so contacted and wherein the ionic impurity is predominantly HBr.

14. The process of claim 13 wherein the temperature is in a range of from about 120° C. to about 170° C.

15. The process of claim 14 wherein the time is in a range of from about 30 seconds to about 1 hour.

16. The improvement of claim 13 wherein the treated water has a resistivity of greater than about 100,000 ohms.

17. The process of claim 13 wherein the amount of treated water is more than about 0.3 grams of water per gram of product so contacted.

18. The improvement of claim 13 wherein the treated water has a resistivity of greater than about 100,000 ohms.

19. The process of claim 18 wherein the amount of ionic impurity in the contacted and heat treated product is less than about 10 ppm.

* * * * *

UNITED STATES PATENT AND TRADEMARK OFFICE
CERTIFICATE OF CORRECTION

PATENT NO. : 5,208,389
DATED : May 4, 1993
INVENTOR(S) : Bonnie G. McKinnie and Gary L. Sharp It is certified that error appears in the above-indentified patent and that said Letters Patent is hereby corrected as shown below:

Column 7, lines 51-52, change "and a temperature" to --and at a temperature--

Signed and Sealed this

Tenth Day of May, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,208,389
DATED : May 4, 1993
INVENTOR(S) : Bonnie G. McKinnie, et al.

It is certified that error appears in the above-indentified patent and that said Letters Patent is hereby corrected as shown below:

Column 8, Line 12, reads "... claim 1 ..." and should read -- ... Claim 7 ... --.

Column 8, Line 15, reads "... claim 1 ..." and should read -- ... Claim 8 ... --.

Column 8, Line 56, reads "... claim 13 ..." and should read -- ... Claim 17 ... --.

Signed and Sealed this

Eleventh Day of October, 1994

Attest:

BRUCE LEHMAN

*Attesting Officer*  *Commissioner of Patents and Trademarks*